(12) United States Patent
Truckai et al.

(10) Patent No.: US 7,621,952 B2
(45) Date of Patent: Nov. 24, 2009

(54) IMPLANTS AND METHODS FOR TREATING BONE

(75) Inventors: Csaba Truckai, Saratoga, CA (US); John H. Shadduck, Tiburon, CA (US)

(73) Assignee: DFINE, Inc., San Jose, CA (US)

( * ) Notice: Subject to any disclaimer, the term of this patent is extended or adjusted under 35 U.S.C. 154(b) by 10 days.

(21) Appl. No.: 11/146,893

(22) Filed: Jun. 7, 2005

(65) Prior Publication Data

US 2006/0089715 A1    Apr. 27, 2006

Related U.S. Application Data

(60) Provisional application No. 60/577,559, filed on Jun. 7, 2004.

(51) Int. Cl.
*A61F 2/44* (2006.01)
(52) U.S. Cl. .................................. 623/17.11
(58) Field of Classification Search .............. 623/16.11, 623/17.11–17.16; 606/61
See application file for complete search history.

(56) References Cited

U.S. PATENT DOCUMENTS

| | | | | |
|---|---|---|---|---|
| 4,291,608 A | * | 9/1981 | Lang et al. | 411/16 |
| 4,536,115 A | * | 8/1985 | Helderman | 411/17 |
| 4,861,206 A | * | 8/1989 | Riedel | 411/36 |
| 5,292,362 A | | 3/1994 | Bass et al. | |
| 5,334,626 A | | 8/1994 | Lin | |
| 5,360,450 A | * | 11/1994 | Giannini | 623/21.19 |
| 5,665,122 A | * | 9/1997 | Kambin | 623/17.16 |
| 5,676,700 A | | 10/1997 | Black et al. | |
| 6,129,763 A | * | 10/2000 | Chauvin et al. | 623/17.11 |
| 6,171,312 B1 | | 1/2001 | Beaty | |
| 6,231,615 B1 | | 5/2001 | Preissman | |
| 6,235,043 B1 | | 5/2001 | Reiley et al. | |
| 6,280,456 B1 | | 8/2001 | Scribner et al. | |
| 6,309,420 B1 | | 10/2001 | Preissman | |
| 6,348,679 B1 | | 2/2002 | Ryan et al. | |
| 6,375,659 B1 | | 4/2002 | Erbe et al. | |

(Continued)

FOREIGN PATENT DOCUMENTS

WO    WO 02/87416    4/2002

(Continued)

OTHER PUBLICATIONS

International Search Report, mailing date May 31, 2006, PCT/US2005/044055, 4 pg.

(Continued)

*Primary Examiner*—Eduardo C Robert
*Assistant Examiner*—Tara R George
(74) *Attorney, Agent, or Firm*—Knobbe, Martens, Olson & Bear LLP

(57) ABSTRACT

An orthopedic implant comprising a deformable, expandable implant body configured for treating abnormalities in bones, such as compression fractures of vertebra, necrosis of femurs and the like. An exemplary implant body comprises a small cross-section threaded element that is introduced into a bone region and thereafter is expanded into a larger cross-section, monolithic assembly to provide a bone support. In one embodiment, the implant body is at least partly fabricated of a magnesium alloy that is biodegradable to allow for later tissue ingrowth.

30 Claims, 8 Drawing Sheets

U.S. PATENT DOCUMENTS

| | | | |
|---|---|---|---|
| 6,436,140 B1 * | 8/2002 | Liu et al. | 623/17.11 |
| 6,458,127 B1 | 10/2002 | Truckai et al. | |
| 6,458,375 B1 | 10/2002 | Gertzman et al. | |
| 6,607,557 B1 | 8/2003 | Brosnahan et al. | |
| 6,620,185 B1 | 9/2003 | Harvie et al. | |
| 6,620,196 B1 | 9/2003 | Trieu | |
| 6,649,888 B2 | 11/2003 | Ryan et al. | |
| 6,740,093 B2 | 5/2004 | Hochschuler et al. | |
| 6,767,350 B1 * | 7/2004 | Lob | 606/63 |
| 6,790,233 B2 | 9/2004 | Brodke et al. | |
| 6,814,736 B2 | 11/2004 | Reiley et al. | |
| 6,835,206 B2 * | 12/2004 | Jackson | 623/17.11 |
| 6,955,691 B2 * | 10/2005 | Chae et al. | 623/17.16 |
| 6,979,352 B2 | 12/2005 | Reynolds | |
| 6,985,061 B2 | 1/2006 | Hafskjold et al. | |
| 7,014,658 B2 * | 3/2006 | Ralph et al. | 623/17.13 |
| 7,044,954 B2 | 5/2006 | Reiley et al. | |
| 7,153,306 B2 | 12/2006 | Ralph et al. | |
| 7,189,263 B2 | 3/2007 | Erbe et al. | |
| 2002/0026195 A1 | 2/2002 | Layne et al. | |
| 2002/0032447 A1 | 3/2002 | Weikel et al. | |
| 2002/0082608 A1 | 6/2002 | Reiley et al. | |
| 2002/0123750 A1 | 9/2002 | Eisermann et al. | |
| 2002/0147497 A1 | 10/2002 | Belef et al. | |
| 2002/0156483 A1 | 10/2002 | Voellmicke et al. | |
| 2002/0177866 A1 | 11/2002 | Weikel et al. | |
| 2002/0183851 A1 | 12/2002 | Spiegelberg et al. | |
| 2003/0055511 A1 | 3/2003 | Schryver et al. | |
| 2003/0130373 A1 | 7/2003 | Walz et al. | |
| 2003/0130738 A1 | 7/2003 | Hovda et al. | |
| 2003/0199980 A1 | 10/2003 | Siedler | |
| 2003/0220648 A1 | 11/2003 | Osorio et al. | |
| 2003/0233096 A1 | 12/2003 | Osorio et al. | |
| 2004/0006347 A1 | 1/2004 | Sproul | |
| 2004/0024410 A1 | 2/2004 | Olson, Jr. et al. | |
| 2004/0092948 A1 | 5/2004 | Stevens et al. | |
| 2004/0097390 A1 | 5/2004 | Justis et al. | |
| 2004/0167561 A1 | 8/2004 | Boucher et al. | |
| 2004/0172058 A1 | 9/2004 | Edwards et al. | |
| 2004/0172132 A1 | 9/2004 | Ginn | |
| 2004/0193171 A1 | 9/2004 | DiMauro et al. | |
| 2004/0225296 A1 | 11/2004 | Reiss et al. | |
| 2004/0228898 A1 | 11/2004 | Ross et al. | |
| 2004/0267271 A9 | 12/2004 | Scribner et al. | |
| 2005/0059979 A1 | 3/2005 | Yetkinler et al. | |
| 2005/0079088 A1 | 4/2005 | Wirth et al. | |
| 2005/0209595 A1 | 9/2005 | Karmon | |
| 2005/0222681 A1 | 10/2005 | Richley et al. | |
| 2005/0245938 A1 | 11/2005 | Kochan | |
| 2005/0261781 A1 | 11/2005 | Sennett et al. | |
| 2006/0052743 A1 | 3/2006 | Reynolds | |
| 2006/0052794 A1 | 3/2006 | McGill et al. | |
| 2006/0052873 A1 | 3/2006 | Buck et al. | |
| 2006/0074433 A1 | 4/2006 | McGill et al. | |
| 2006/0079905 A1 | 4/2006 | Beyar et al. | |
| 2006/0085009 A1 | 4/2006 | Truckai et al. | |
| 2006/0085081 A1 | 4/2006 | Truckai et al. | |
| 2006/0089715 A1 | 4/2006 | Truckai et al. | |
| 2006/0100635 A1 | 5/2006 | Reiley et al. | |
| 2006/0106459 A1 | 5/2006 | Truckai et al. | |
| 2006/0122621 A1 | 6/2006 | Truckai et al. | |
| 2006/0122622 A1 | 6/2006 | Truckai et al. | |
| 2006/0122623 A1 | 6/2006 | Truckai et al. | |
| 2006/0122624 A1 | 6/2006 | Truckai et al. | |
| 2006/0122625 A1 | 6/2006 | Truckai et al. | |
| 2006/0198865 A1 | 9/2006 | Freyman et al. | |
| 2006/0229625 A1 | 10/2006 | Truckai et al. | |
| 2006/0264965 A1 | 11/2006 | Shadduck et al. | |
| 2006/0264967 A1 | 11/2006 | Ferreyro et al. | |
| 2006/0265077 A1 | 11/2006 | Zwirkoski | |
| 2007/0162043 A1 | 7/2007 | Truckai et al. | |
| 2007/0225705 A1 | 9/2007 | Osorio et al. | |
| 2007/0233146 A1 | 10/2007 | Henniges et al. | |
| 2007/0233249 A1 | 10/2007 | Shadduck | |
| 2007/0233250 A1 | 10/2007 | Shadduck | |

FOREIGN PATENT DOCUMENTS

WO    WO 2006/031490      3/2006

OTHER PUBLICATIONS

International Search Report, mailing date Jun. 20, 2006, PCT/US2005/043984, 3 pg.

Carrodeguas, et al., "Injectable Acrylic Bone Cements for Vertebroplasty with Improved Properties", Journal of Biomedical Materials Research, XP002312783, vol. 68, No. 1, Jan. 15, 2004, pp. 94-104.

B. Heublein et al. "Biocorrosion of magnesium alloys: a new principle in cardiovascular implant technology?", *Heart* 2003: 89:651-656.

Office Action dated Nov. 1, 2007 received in U.S. Appl. No. 11/199,582.

Office Action dated Jan. 10, 2008 received in U.S. Appl. No. 11/146,891.

Office Action dated Mar. 28, 2008 received in U.S. Appl. No. 11/267,950.

Office Action dated Apr. 3, 2008 received in U.S. Appl. No. 11/215,730.

* cited by examiner

IMPLANTS AND METHODS FOR TREATING BONE

CROSS-REFERENCE TO RELATED APPLICATIONS

This application claims benefit of Provisional U.S. Patent Application Ser. No. 60/577,559 filed Jun. 7, 2004 titled Reticulated Implants and Methods for Treating Abnormalities in Bone, the entire contents of which are hereby incorporated by reference in their entirety and should be considered a part of this specification.

BACKGROUND OF THE INVENTION

1. Field of the Invention

This invention relates to medical implants and more particularly to expandable open cell reticulated implants configured as bone support implants for treating abnormalities in bones such as compression fractures of vertebra, necrosis of femurs and the like. An exemplary implant body comprises a small cross-section threaded element that is introduced into a bone region and thereafter is expanded into a larger cross-section, open cell reticulated monolith to provide a bone support.

2. Description of the Related Art

Osteoporotic fractures are prevalent in the elderly, with an annual estimate of 1.5 million fractures in the United States alone. These include 750,000 vertebral compression fractures (VCFs) and 250,000 hip fractures. The annual cost of osteoporotic fractures in the United States has been estimated at $13.8 billion. The prevalence of VCFs in women age 50 and older has been estimated at 26%. The prevalence increases with age, reaching 40% among 80-year-old women. Medical advances aimed at slowing or arresting bone loss from aging have not provided solutions to this problem. Further, the affected population will grow steadily as life expectancy increases. Osteoporosis affects the entire skeleton but most commonly causes fractures in the spine and hip. Spinal or vertebral fractures also have serious consequences, with patients suffering from loss of height, deformity and persistent pain which can significantly impair mobility and quality of life. Fracture pain usually lasts 4 to 6 weeks, with intense pain at the fracture site. Chronic pain often occurs when one level is greatly collapsed or multiple levels are collapsed.

Postmenopausal women are predisposed to fractures, such as in the vertebrae, due to a decrease in bone mineral density that accompanies postmenopausal osteoporosis. Osteoporosis is a pathologic state that literally means "porous bones". Skeletal bones are made up of a thick cortical shell and a strong inner meshwork, or cancellous bone, of collagen, calcium salts and other minerals. Cancellous bone is similar to a honeycomb, with blood vessels and bone marrow in the spaces. Osteoporosis describes a condition of decreased bone mass that leads to fragile bones which are at an increased risk for fractures. In an osteoporosic bone, the sponge-like cancellous bone has pores or voids that increase in dimension, making the bone very fragile. In young, healthy bone tissue, bone breakdown occurs continually as the result of osteoclast activity, but the breakdown is balanced by new bone formation by osteoblasts. In an elderly patient, bone resorption can surpass bone formation thus resulting in deterioration of bone density. Osteoporosis occurs largely without symptoms until a fracture occurs.

Vertebroplasty and kyphoplasty are recently developed techniques for treating vertebral compression fractures. Percutaneous vertebroplasty was first reported by a French group in 1987 for the treatment of painful hemangiomas. In the 1990's, percutaneous vertebroplasty was extended to indications including osteoporotic vertebral compression fractures, traumatic compression fractures, and painful vertebral metastasis. In one percutaneous vertebroplasty technique, bone cement such as PMMA (polymethylmethacrylate) is percutaneously injected into a fractured vertebral body via a trocar and cannula system. The targeted vertebrae are identified under fluoroscopy. A needle is introduced into the vertebral body under fluoroscopic control to allow direct visualization. A transpedicular (through the pedicle of the vertebrae) approach is typically bilateral but can be done unilaterally. The bilateral transpedicular approach is typically used because inadequate PMMA infill is achieved with a unilateral approach.

In a bilateral approach, approximately 1 to 4 ml of PMMA are injected on each side of the vertebra. Since the PMMA needs to be forced into cancellous bone, the technique requires high pressures and fairly low viscosity cement. Since the cortical bone of the targeted vertebra may have a recent fracture, there is the potential of PMMA leakage. The PMMA cement contains radiopaque materials so that when injected under live fluoroscopy, cement localization and leakage can be observed. The visualization of PMMA injection and extravasion are critical to the technique—and the physician terminates PMMA injection when leakage is evident. The cement is injected using small syringe-like injectors to allow the physician to manually control the injection pressures.

Kyphoplasty is a modification of percutaneous vertebroplasty. Kyphoplasty involves a preliminary step that comprises the percutaneous placement of an inflatable balloon tamp in the vertebral body. Inflation of the balloon creates a cavity in the bone prior to cement injection. Further, the proponents of percutaneous kyphoplasty have suggested that high pressure balloon-tamp inflation can at least partially restore vertebral body height. In kyphoplasty, it has been proposed that PMMA can be injected at lower pressures into the collapsed vertebra since a cavity exists to receive the cement—which is not the case in conventional vertebroplasty.

The principal indications for any form of vertebroplasty are osteoporotic vertebral collapse with debilitating pain. Radiography and computed tomography must be performed in the days preceding treatment to determine the extent of vertebral collapse, the presence of epidural or foraminal stenosis caused by bone fragment retropulsion, the presence of cortical destruction or fracture and the visibility and degree of involvement of the pedicles. Leakage of PMMA during vertebroplasty can result in very serious complications including compression of adjacent structures that necessitate emergency decompressive surgery.

Leakage or extravasion of PMMA is a critical issue and can be divided into paravertebral leakage, venous infiltration, epidural leakage and intradiscal leakage. The exothermic reaction of PMMA carries potential catastrophic consequences if thermal damage were to extend to the dural sac, cord, and nerve roots. Surgical evacuation of leaked cement in the spinal canal has been reported. It has been found that leakage of PMMA is related to various clinical factors such as the vertebral compression pattern, and the extent of the cortical fracture, bone mineral density, the interval from injury to operation, the amount of PMMA injected and the location of the injector tip. In one recent study, close to 50% of vertebroplasty cases resulted in leakage of PMMA from the vertebral bodies. See Hyun-Woo Do et al, "The Analysis of Polymethylmethacrylate Leakage after Vertebroplasty for Vertebral Body Compression Fractures", Jour. of Korean Neurosurg.

Soc. Vol. 35, No. 5 (May 2004) pp. 478-82, (http://www.jkns.or.kr/htm/abstract.asp?no=0042004086).

Another recent study was directed to the incidence of new VCFs adjacent to the vertebral bodies that were initially treated. Vertebroplasty patients often return with new pain caused by a new vertebral body fracture. Leakage of cement into an adjacent disc space during vertebroplasty increases the risk of a new fracture of adjacent vertebral bodies. See Am. J. Neuroradiol. 2004 February; 25(2): 175-80. The study found that 58% of vertebral bodies adjacent to a disc with cement leakage fractured during the follow-up period compared with 12% of vertebral bodies adjacent to a disc without cement leakage.

Another life-threatening complication of vertebroplasty is pulmonary embolism. See Bernhard, J. et al., "Asymptomatic diffuse pulmonary embolism caused by acrylic cement: an unusual complication of percutaneous vertebroplasty", Ann. Rheum. Dis. 2003; 62:85-86. The vapors from PMMA preparation and injection are also cause for concern. See Kirby, B., et al., "Acute bronchospasm due to exposure to polymethylmethacrylate vapors during percutaneous vertebroplasty", Am. J. Roentgenol. 2003; 180:543-544.

Another disadvantage of PMMA is its inability to undergo remodeling—and the inability to use the PMMA to deliver osteoinductive agents, growth factors, chemotherapeutic agents and the like. Yet another disadvantage of PMMA is the need to add radiopaque agents which lower its viscosity with unclear consequences on its long-term endurance.

In both higher pressure cement injection (vertebroplasty) and balloon-tamped cementing procedures (kyphoplasty), the methods do not provide for well controlled augmentation of vertebral body height. The direct injection of bone cement simply follows the path of least resistance within the fractured bone. The expansion of a balloon also applies compacting forces along lines of least resistance in the collapsed cancellous bone. Thus, the reduction of a vertebral compression fracture is not optimized or controlled in high pressure balloons as forces of balloon expansion occur in multiple directions.

In a kyphoplasty procedure, the physician often uses very high pressures (e.g., up to 200 or 300 psi) to inflate the balloon which first crushes and compacts cancellous bone. Expansion of the balloon under high pressures close to cortical bone can fracture the cortical bone, or cause regional damage to the cortical bone that can result in cortical bone necrosis. Such cortical bone damage is highly undesirable and results in weakened cortical endplates.

Kyphoplasty also does not provide a distraction mechanism capable of 100% vertebral height restoration. Further, the kyphoplasty balloons under very high pressure typically apply forces to vertebral endplates within a central region of the cortical bone that may be weak, rather than distributing forces over the endplate.

There is a general need to provide systems and methods for use in treatment of vertebral compression fractures that provide a greater degree of control over introduction of bone support material, and that provide better outcomes. Embodiments of the present invention meet one or more of the above needs, or other needs, and provide several other advantages in a novel and non-obvious manner.

SUMMARY OF THE INVENTION

The invention provides a method of correcting numerous bone abnormalities including vertebral compression fractures, bone tumors and cysts, avascular necrosis of the femoral head and the like. The abnormality may be corrected by first accessing and boring into the damaged tissue or bone (FIG. 1). Thereafter, the implant body is advanced into the bore, wherein successive axial segments of the implant engage one another to provide radial expansion of the implant. The implant system eliminates the need to ream, compact, tamp or otherwise treat the bone region before the insertion of the implant assembly.

BRIEF DESCRIPTION OF THE DRAWINGS

In the following detailed description, similar reference numerals are used to depict like elements in the various figures.

DETAILED DESCRIPTION OF THE INVENTION

Figure 2A:
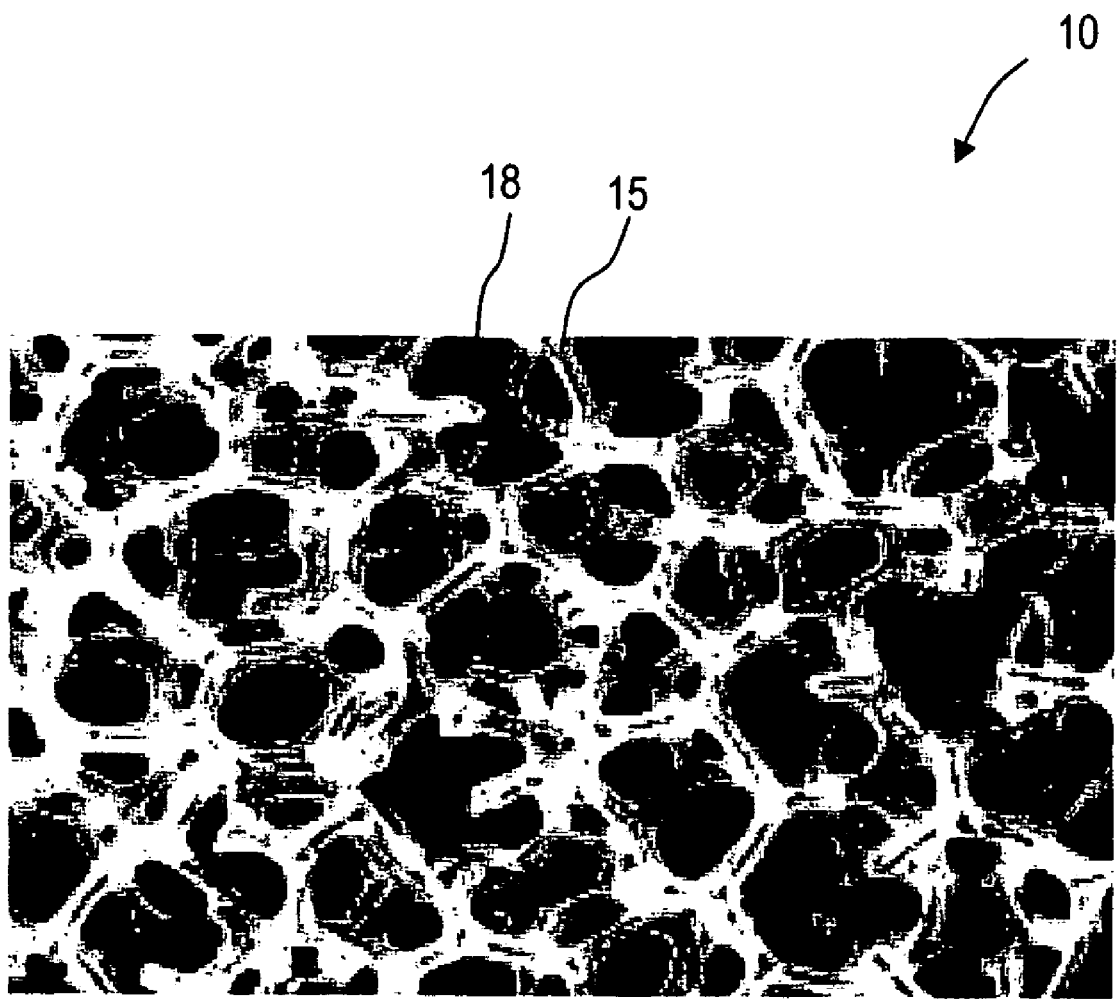
FIG. 2A is a greatly enlarged view of the reticulated material of the expandable implants corresponding to the invention.

The present invention comprises a bone implant of a reticulated material that can be radially expanded in cross-section to support a bone, and more particularly to move apart cortical endplates to at leat partly restore vertebral height. In one embodiment, the implants elements comprise reticulated scaffold structures that can allow for later bone ingrowth. FIG. 2A illustrates a greatly enlarged view of an exemplary open cell reticulated material 10 corresponding to the invention that is useful for defining terms used herein to describe the implants. In general, the term reticulated means having the appearance of, or functioning as wire network or substantially rigid net structure. The related term reticulate mean resembling or forming a network. The terms reticulated, reticulate and trabecular are used interchangeably herein to describe structures having ligaments 15 that bound an open cells 18 or closed cell in the interior structure.

Such reticulated structures 10 as in FIG. 2A are further defined by density—which describes the ligament volume as a percentage of a solid. In other words, the density defines the volume of material relative to the volume of open cells in a monolith of the base material. As density of the ligaments increase with larger cross-sections and smaller cell dimensions, the elastic modulus of the material will increase.

The cells of reticulated structure 10 (FIG. 2A) also define a mean cross section which can be expressed in microns. In preferred embodiments, the cells are bounded by polyhedral faces, typically pentagonal or hexagonal, that are formed with five or six ligaments 15. Cell dimension is selected for enhancing tissue ingrowth, and mean cell cross-sections can range between 10 micron and 300 microns; and more preferably ranges between 20 microns and 200 microns.

Figure 1:
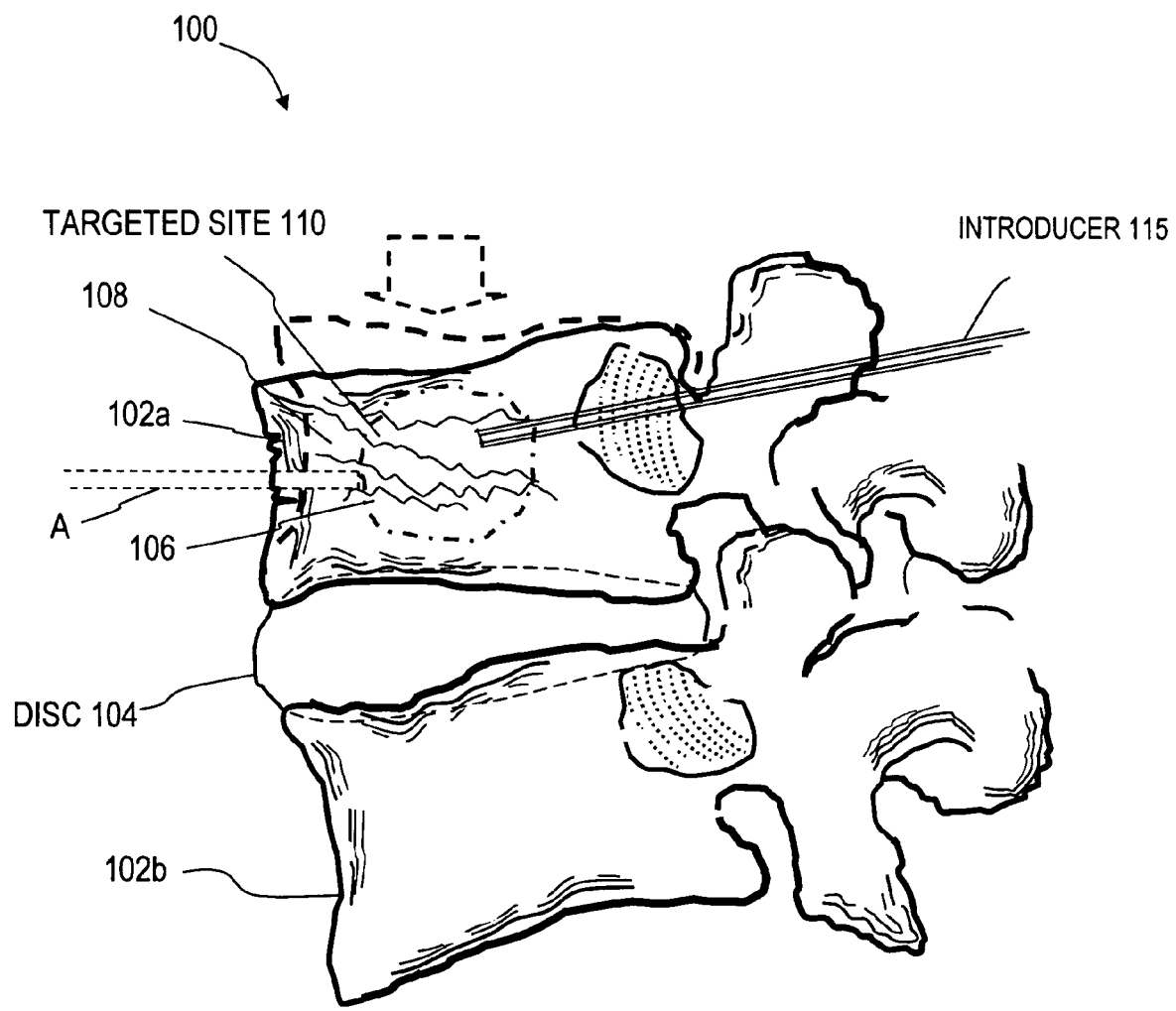
FIG. 1 is a side view of a segment of a spine with a vertebral compression fracture that can be treated with the present invention, showing an introducer in posterior access path to the targeted treatment site.

In general, the system and method of invention relates to minimally invasive percutaneous interventions for providing bone support with an implant scaffold that is expanded in situ into a rigid, reticulated monolithic body. FIG. 1 illustrates a spine segment 100 with vertebrae 102*a* and 102*b* and disc 104. The vertebra 102*a* and cancellous bone 106 therein is depicted as having suffered a compression fracture 108 that can be repaired with the present invention. The targeted treatment region 110 (FIG. 1) can be accessed in either posterior or anterior approach A with a minimally invasive access pathway, for example with an introducer 115 having a 5 mm. or smaller diameter. In other embodiments, the introducer and implants are preferably less than about 3 mm. in cross-section.

Figure 2B:
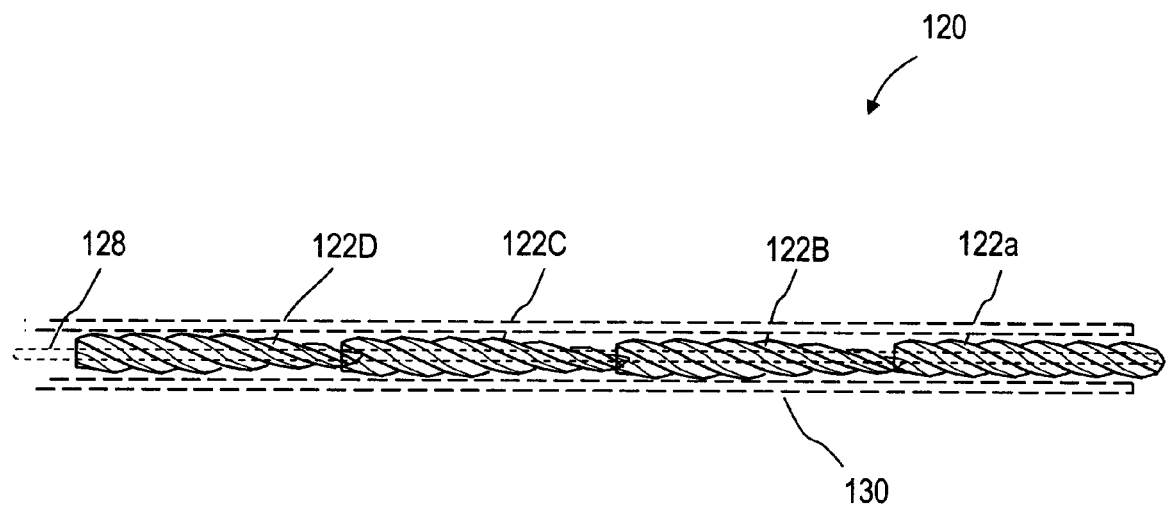
FIG. 2B is a side view of a segmented reticulated implant body corresponding to the invention.

Now referring to FIG. 2B, an exemplary radially expandable implant body 120 is illustrated in a first pre-deployed configuration. In this configuration, it can be seen that the elongate body 120 comprises a plurality of axial-extending segments 122*a*-122*d* that extend along axis 125. In a preferred embodiment, the segments 122*a*-122*d* are linked by break-away joints. Alternatively, the segments are cannulated and carried about a shaft indicated at 128. As another alternative, the segments 122*a*-122*d* are independent bodies that are introduced sequentially through introducer sleeve 130. The segments 122*a*-122*d* are configured for axial segment-to-segment insertion to thereby radially expand the assembled implant body. The expandable implant can includes from 2 to 20 body segments.

As illustrated in FIG. 2B, the radially expandable implant body 120 is housed in an introducer 130 that comprises a sleeve extending from a handle (not shown). The introducer and handle carry a rotational/helical advancement mechanism for engaging the proximal end 132 of the implant, and preferably includes a motor-driven mechanism.

Figures 3A, 3B:
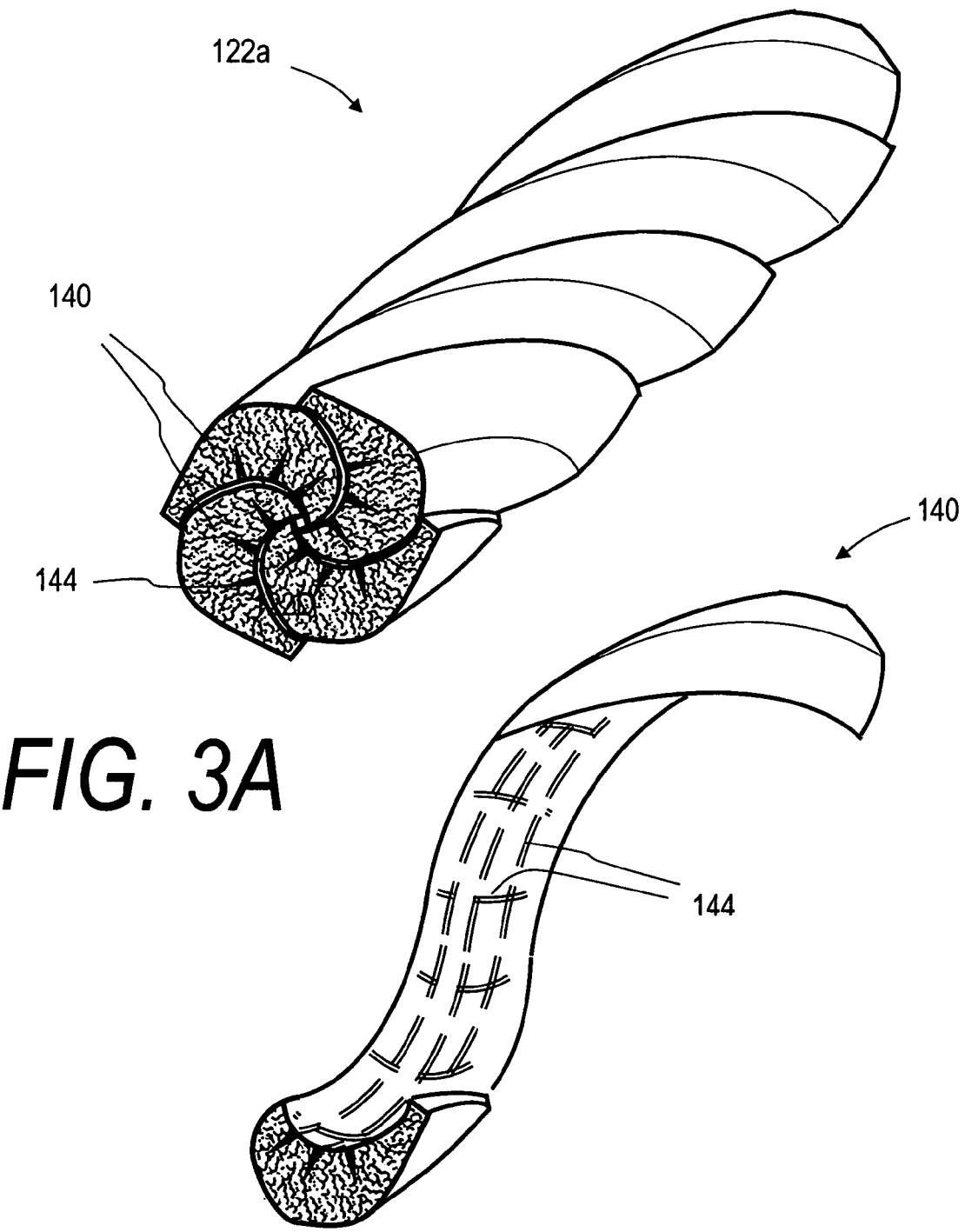
FIG. 3A is a sectional perspective view of one of the reticulated implant segments of FIG. 2B taken along line 3-3 of FIG. 2B.
FIG. 3B is a view of a helical element that is a component of the reticulated implant segment as in FIG. 3A.

FIGS. 3A and 3B are views of a segment 122*a* of the radially expandable implant body 120. In FIG. 3A, it can be seen that each segment consists of a plurality of segment subcomponents or elements 140 (collectively) that are configured to helically intertwine.

FIG. 3B illustrates a single segment element 140 de-mated from the cooperating elements. The element is of a metal or polymer that is somewhat deformable. The elements can further be configured with weakened planes, relaxing cuts, hinge or flex portions 144 or the like to allow bending of the elements to permit controlled deformation and expansion of the body. In preferred embodiments, the expandable implant 120 has segments with a surface spiral thread. In another preferred embodiment, the hinge or flex portions 144 comprise flexible reticulated (open cell) polymer that couples together the rigid reticulated metal portions. Thus, the scope of the invention includes for the first time inventive means for fabricating a deformable but non-collapsible reticulated implant body.

The elements 140 are fabricated of a reticulated material 100 (FIG. 3A) that has a ligament density ranging between 20 percent and 90 percent. More preferably, the reticulated material has a ligament density ranging between 20 percent and 50 percent. In one embodiment, the reticulated material includes titanium, tantalum, stainless steel or a magnesium alloy that is biodegradable. In another embodiment, the reticulated material is at least partly a polymer, which can be at least one of bioerodible, bioabsorbable or bioexcretable.

Figure 4A:
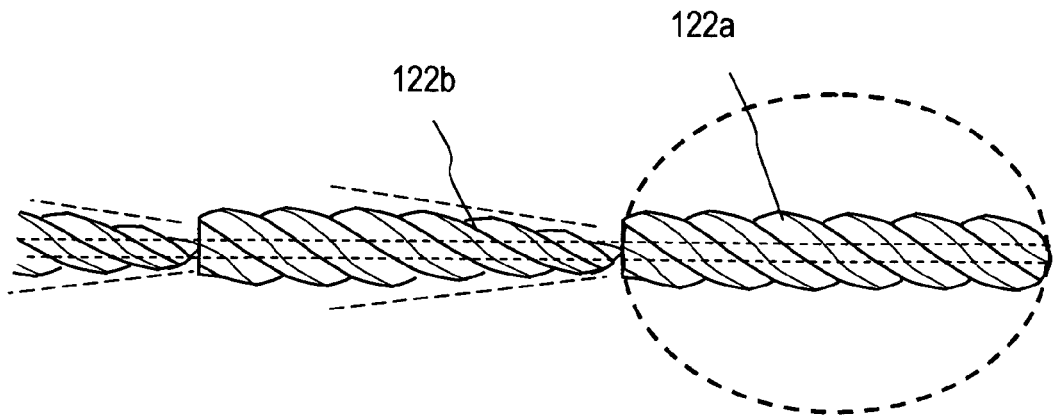
FIGS. 4A-4C are schematic views of a method of the invention in treating a fracture as depicted in FIG. 1.
Figure 4B:
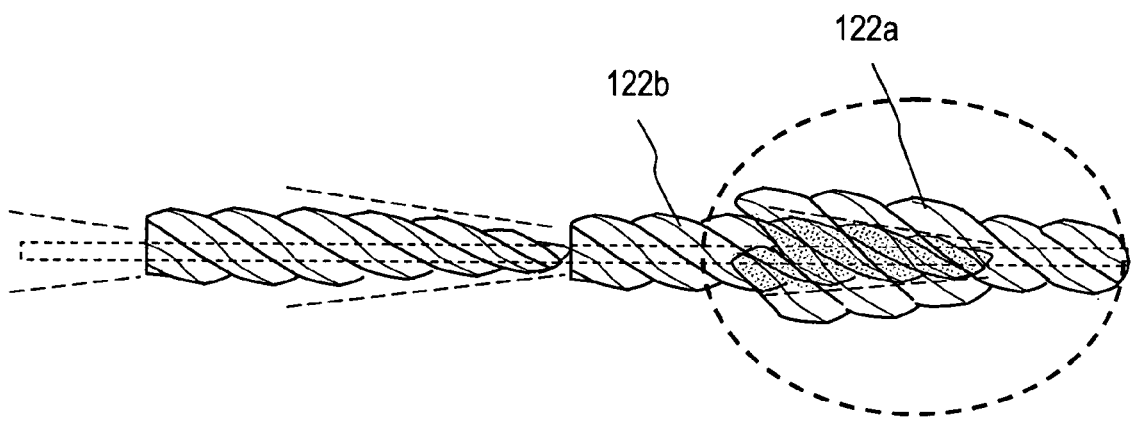
Figure 4C:
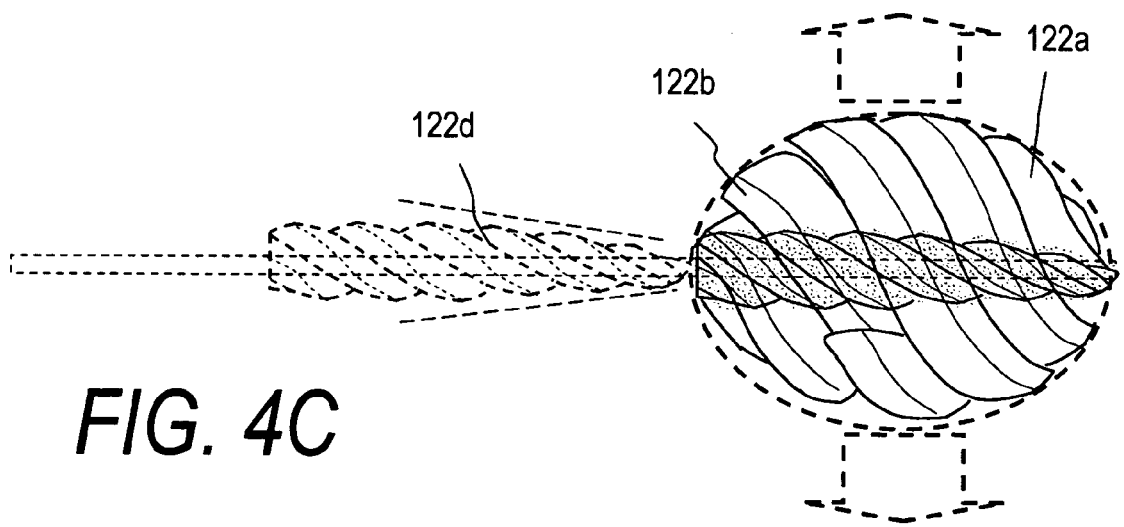

FIGS. 4A-4C illustrate an exemplary sequence of utilizing a 3 or 4 segment implant to create a radially expanded reticulated monolith 120'. For example, a pre-deployed implant as in FIG. 2B can have a diameter of about 4 mm and can be expanded to a selected oval or roughly spherical shape having a diameter of 12 to 16 mm. The expandable, reticulated segments can have common right-hand or left-hand surface spiral thread configurations. Alternatively, the segments can have different right-hand and left-hand surface spiral thread configurations.

It can be easily understood that an expandable implant can have variable open cell cross sections, or a radial gradient in open cell cross sections by providing different segment with different densities and cell dimension.

An expandable implant also can have reticulated material provided with open cells filled with an infill polymer. Such an infill polymer is at least one of bioerodible, bioabsorbable or bioexcretable.

Figure 6:
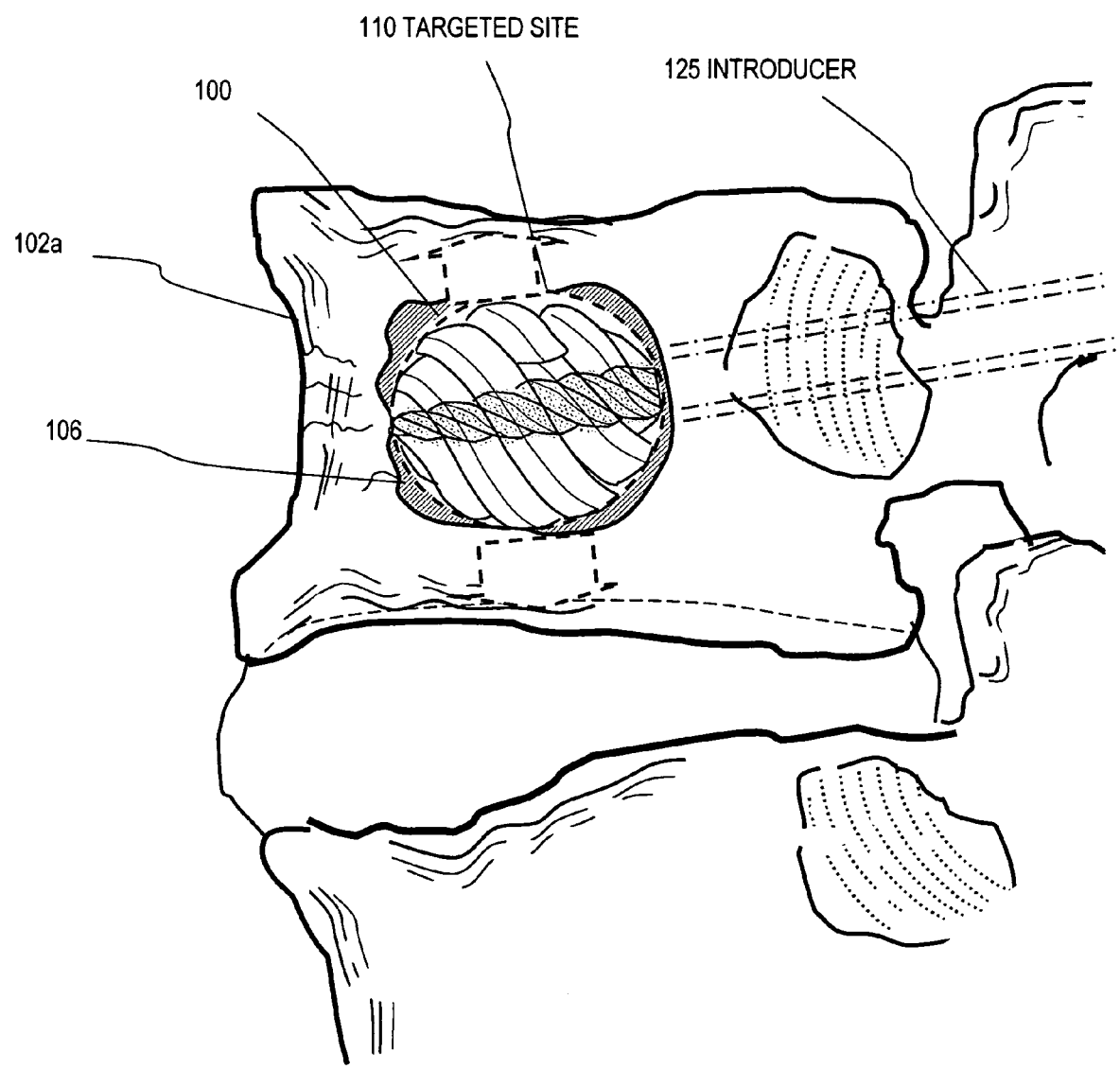
FIG. 6 is a schematic view of the damaged vertebra of FIG. 1 with the reticulated implant monolith I in place after expanding the height of the damaged vertebrae and providing a reticulated scaffold therein.

The method of the invention include treating, or prophylactically preventing, a fracture in a bone structure and comprised the steps of introducing a reticulated body of a deformable reticulated elements in a first cross-sectional dimension into the bone structure. Thereafter, the implant body is expanding into a reticulated monolith to a second increased cross-sectional dimension as depicted in FIG. 6. The method includes expanding the implant to replace or displace trabecular bone with the reticulated body. The method includes expanding the implant to support cortical bone adjacent the reticulated body, and to jack apart the cortical vertebral endplates.

Figure 5A:
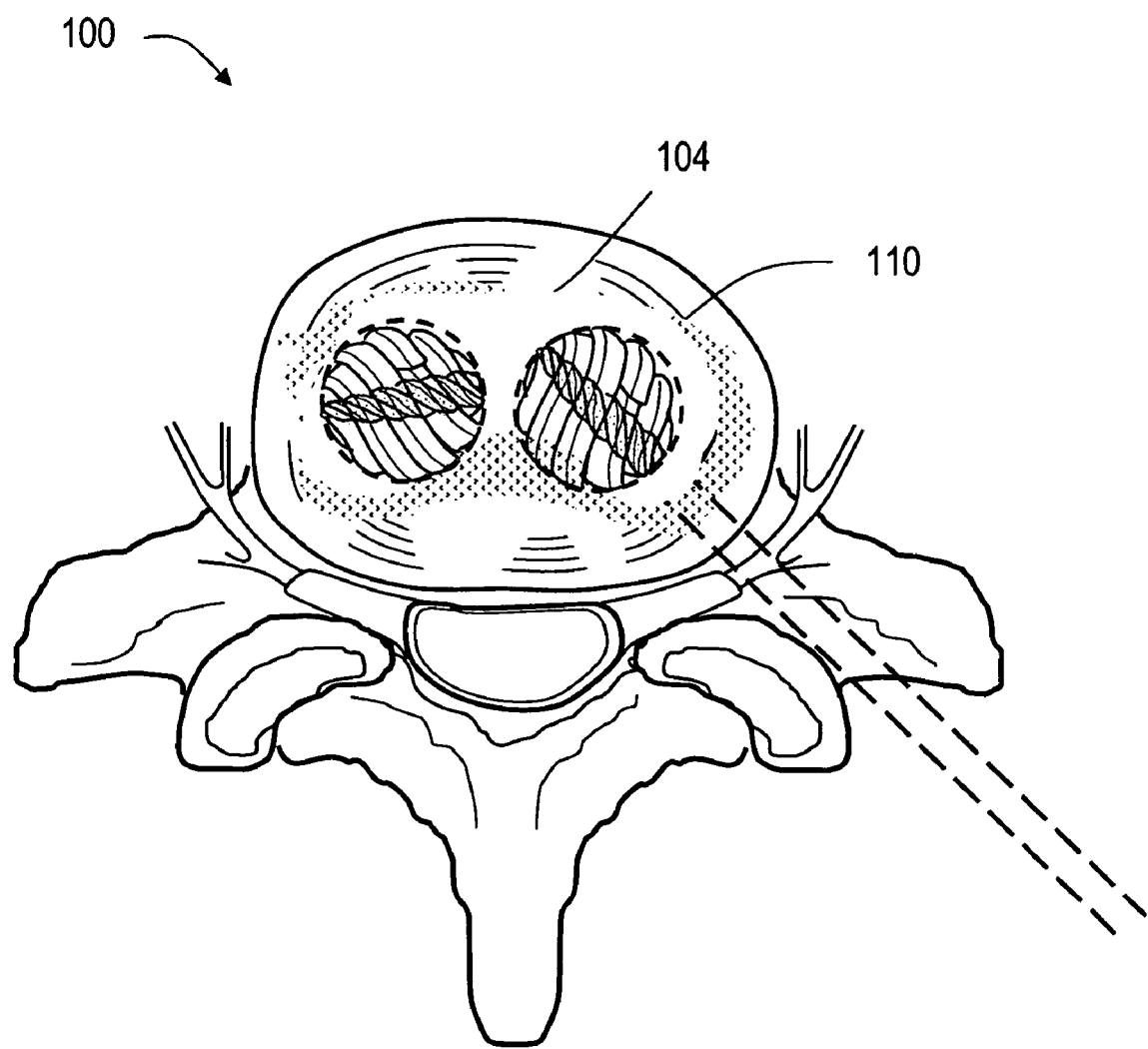
FIG. 5A is a cross-sectional view of the vertebra and fracture of FIG. 1 with multiple implants deployed in a targeted region from a single access.
Figure 5B:
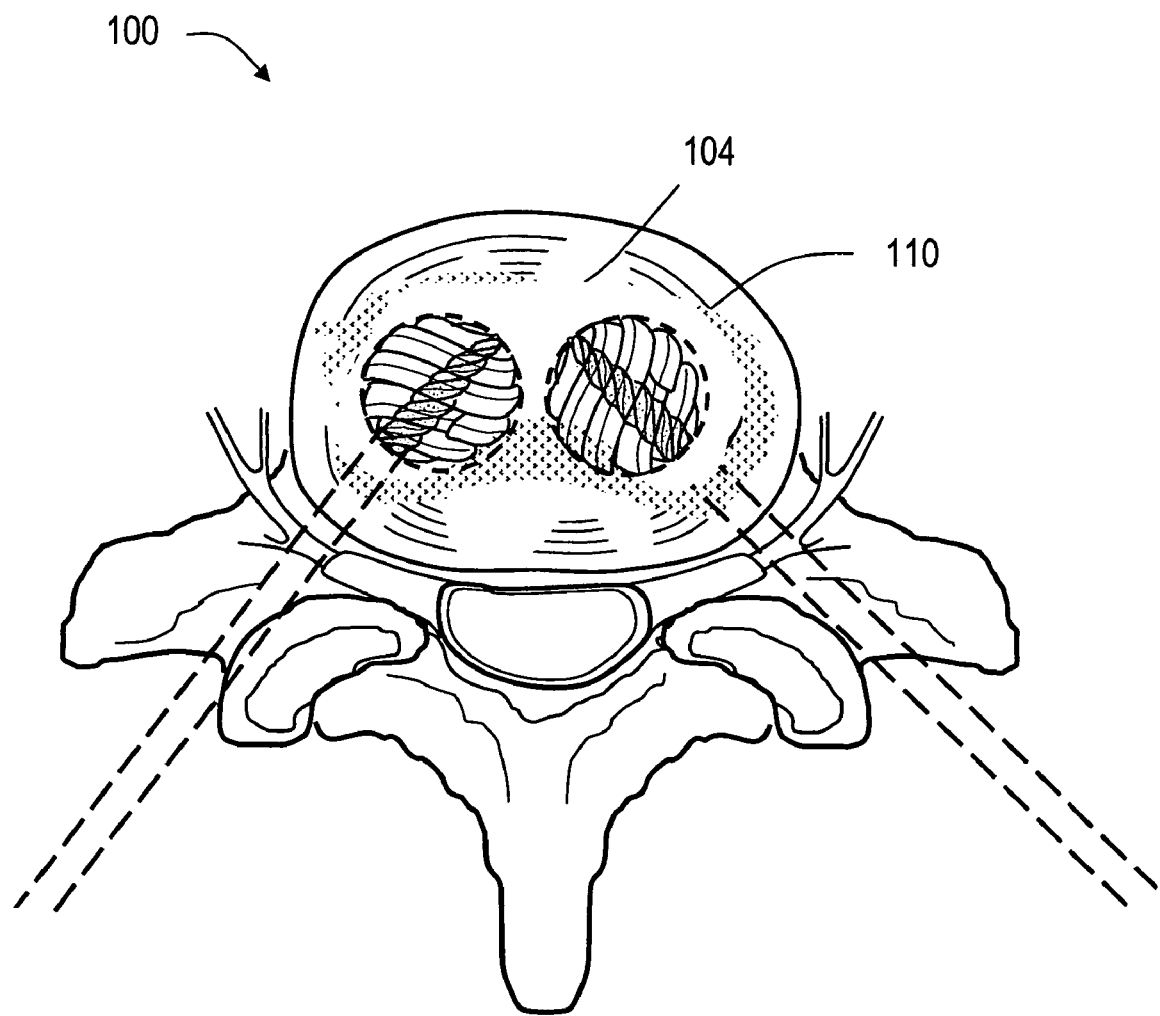
FIG. 5B is a cross-sectional view of the vertebra and fracture of FIG. 1 with multiple implants deployed from two access paths.

Of particular interest, the expandable implant may be used in a prophylactic manner with small introducers, for example, to provide bone support in vertebrae of patients in advance of compression fracture. FIGS. 5A and 5B indicate that the treatment site 110 can be a single region accessed from a single access pathway or multiple spaced apart regions, for example accessed by two minimally invasive access pathways.

The expandable implant of the invention also can be used as a fusion implant to controllably expand in an intervertebral space to controllably engage first and second vertebral bodies. The system allows for less invasive access to a targeted site for such a fusion implant.

Reticulated metals are available from ERG Materials and Aerospace Corp., 900 Stanford Avenue, Oakland Calif. 94608 or Porvair Advanced Materials, Inc., 700 Shepherd Street, Hendersonville N.C. 28792.

In any embodiment, the implant segments 122*a*-112*d* further can carry a radiopaque composition if the material of the implant itself is not radiovisible.

In any embodiment, the segments further can carry any pharmacological agent or any of the following: antibiotics, cortical bone material, synthetic cortical replacement material, demineralized bone material, autograft and allograft materials. The implant body also can include drugs and agents for including bone growth, such as bone morphogenic protein (BMP). The implants can carry the pharmacological agents for immediate or timed release.

The above description of the invention intended to be illustrative and not exhaustive. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed:

1. An expandable implant, comprising:
an elongated body configured for insertion into or adjacent a bone in a collapsed configuration and moveable into an expanded configuration to support the bone, the body comprising a plurality of similarly shaped body segments aligned with each other along an axis in the collapsed configuration, at least one of the body segments insertable along the axis into a second of the body segments so as to helically unwind the second body segment in a direction outward from the axis to thereby controllably move the body into the expanded configuration, each of the body segments comprising at least one deformable element wound about the axis along the length of the body segment from a proximal end to a distal end of the body segment, said at least one element configured to unwind outward from the axis upon the introduction of said at least one body segment into the second body segment 2. An expandable implant as in claim 1, wherein the at least one element is at least partly of a metal.

3. An expandable implant as in claim 2, wherein the metal includes at least one of titanium, tantalum or a magnesium alloy.

4. An expandable implant as in claim 1, wherein the at least one element is at least partly of a polymer.

5. An expandable implant as in claim 4, wherein the polymer is at least one of biodegradable, bioabsorbable or bioexcretable.

6. An expandable implant as in claim 1, wherein the plurality of body segments are configured for axial segment-to-segment insertion to thereby radially expand the elongated body.

7. An expandable implant as in claim 6, wherein the body includes from 2 to 10 body segments.

8. An expandable implant as in claim 6, wherein each of the body segments has a spiral thread surface.

9. An expandable implant as in claim 8, wherein the body segments have a common right-hand or left-hand spiral thread surface.

10. An expandable implant as in claim 8, wherein body segments have different right-hand and left-hand surface spiral thread surfaces.

11. An expandable implant as in claim 1, wherein the body has an open cell structure.

12. A method of treating or prophylactically preventing a fracture of a bone comprising:
introducing into a bone a first implant body segment comprising a deformable helical segment extending about an axis of the first implant body segment, the deformable helical segment being expandable in a direction generally orthogonal to the axis, at least a portion of the deformable helical element contacting the bone; and
introducing at least two additional implant body segments into the interior of the first body segment to thereby helically unwind the helical segment of the first implant body segment outward from the axis to radially expand the first implant body segment in a direction perpendicular to the axis to support the bone.

13. The method of claim 12, wherein introducing the implant body segments displaces cancellous bone.

14. The method of claim 12, wherein introducing the implant body segments moves cortical bone.

15. The method of claim 12, wherein the bone is a vertebra.

16. The method of claim 14, wherein introducing the implant body segments at least partially restores vertebral height.

17. A method for treating an abnormality in a bone comprising:
introducing an implant body into a bone wherein the implant body includes a biodegradable magnesium alloy expanding the implant body within bone, wherein expanding the implant body comprises axially inserting at least two implant segments into a third implant segment to radially expand the third implant segment outward from the axis, wherein radially expanding the third implant segment comprises helically deforming the third implant segment; and
allowing the magnesium alloy to biodegrade thereby creating space for tissue ingrowth.

18. The method of claim 17, wherein the implant body is deformable and further including the step of radially expanding the deformable implant body.

19. The method of claim 17, wherein the implant body is configured for implantation in a vertebra, and introducing the implant body into a bone includes introducing substantially the entire implant body into a vertebra.

20. The expandable implant of claim 1, wherein the elongated body in the collapsed configuration has a cross-section generally perpendicular to the axis of about 4 mm.

21. The expandable implant of claim 1, wherein the elongated body in the expanded configuration has a cross-section generally perpendicular to the axis of between about 12 mm and about 16 mm.

22. The implant of claim 1, wherein the elongated body is configured for insertion in an intervertebral space.

23. The implant of claim 1, wherein the plurality of similarly shaped body segments aligned with each other along the axis in the collapsed configuration are coupled together via break-away joints.

24. The method of claim 12, wherein the at least two additional implant body segments are deformable helical segments.

25. The method of claim 12, wherein helically deforming the helical segment of the first implant body comprises demating and spacing apart helically-mated elements of the helical segment.

26. The method of claim 12, wherein introducing the at least two additional implant body segments into the first body segment comprises breaking a break-away joint between the additional implant body segments and the first body segment.

27. An expandable implant insertable into a vertebra, comprising:
an elongated body configured for insertion into a vertebral body along an axis in a collapsed configuration and moveable into an expanded configuration, the body defined by at least three similarly shaped radially deformable segments aligned end-to-end with each other, at least a first and a second segment axially insertable into a third segment such that an outer surface of the first segment helically contacts an inner surface of the third segment to thereby untwist the third segment and expand the body radially outward from the axis.

28. The implant of claim 27, wherein each of the deformable segments comprises a plurality of dematable helically-mated elements intertwined with each other about the axis.

29. The implant of claim 27, wherein each of the deformable segments comprises a spiral thread surface on an outer surface of the deformable segment.

30. The implant of claim 1, wherein each body segment comprises a plurality of elements wound about the axis, said plurality of elements configured to unwind upon the introduction of said at least one body segment into the second body segment.

* * * * *

UNITED STATES PATENT AND TRADEMARK OFFICE
CERTIFICATE OF CORRECTION

PATENT NO. : 7,621,952 B2
APPLICATION NO. : 11/146893
DATED : November 24, 2009
INVENTOR(S) : Csaba Truckai et al.

It is certified that error appears in the above-identified patent and that said Letters Patent is hereby corrected as shown below:

Column 1, line 56, Change "osteoporosic" to --osteoporotic--.

Column 2, line 25, Change "extravasion" to --extravasation--.

Column 2, line 52, Change "extravasion" to --extravasation--.

Column 4, line 5, Change "to" to --the--.

Column 4, line 46, Change "leat" to --least--.

Column 6, line 57, Change "including" to --inducing--.

Column 7, line 20, In Claim 1, change "segment" to --segment.--.

Column 8, line 4, In Claim 17, change "alloy" to --alloy;--.

Signed and Sealed this

Eighth Day of June, 2010

David J. Kappos
*Director of the United States Patent and Trademark Office*